(12) United States Patent
Menage (10) Patent No.: US 9,518,912 B2
(45) Date of Patent: Dec. 13, 2016

(54) PERMEABILITY DETERMINATION

(71) Applicant: Industrial Textiles & Plastics Ltd, Yorkshire (GB)

(72) Inventor: Richard R. Menage, Yorkshire (GB)

(73) Assignee: Industrial Textiles & Plastics Ltd., Yorkshire (GB)

( * ) Notice: Subject to any disclaimer, the term of this patent is extended or adjusted under 35 U.S.C. 154(b) by 227 days.

(21) Appl. No.: 14/311,863

(22) Filed: Jun. 23, 2014

(65) Prior Publication Data

US 2014/0373601 A1    Dec. 25, 2014

(30) Foreign Application Priority Data

Jun. 24, 2013 (GB) .................................. 1311203.2

(51) Int. Cl.
    *G03G 15/08* (2006.01)
    *G01N 15/08* (2006.01)
    *A62B 17/00* (2006.01)

(52) U.S. Cl.
    CPC .......... *G01N 15/0826* (2013.01); *A62B 17/00* (2013.01); *G01N 15/08* (2013.01)

(58) Field of Classification Search
    CPC ................................................. G01N 15/0826
    USPC ............................................................. 73/38
    See application file for complete search history.

(56) References Cited

U.S. PATENT DOCUMENTS

| | | | | |
|---|---|---|---|---|
| 6,119,506 A | * | 9/2000 | Gibson | G01N 15/0826 34/89 |
| 6,335,202 B1 | | 1/2002 | Lee et al. | |
| 2005/0026294 A1 | | 2/2005 | Barber | |
| 2008/0303658 A1 | * | 12/2008 | Melker | G08B 21/245 340/540 |

OTHER PUBLICATIONS

Search Report issued Nov. 20, 2013, in GB Application No, 1311203.2.

* cited by examiner

*Primary Examiner* — Walter L Lindsay, Jr.
*Assistant Examiner* — Philip Marcus T Fadul
(74) *Attorney, Agent, or Firm* — Andrus Intellectual Property Law, LLP (57) ABSTRACT

Apparatus and methods determine a permeation characteristic of a challenge chemical for a chemical protective material. A processor retrieves barrier characteristics of the chemical protective material for which the permeation characteristic is to be determined from a computer memory. Information regarding the challenge chemical is obtained. A temperature is received of the chemical protective material for which the permeation characteristic is to be determined. The permeation characteristic is determined from the temperature, the barrier characteristics, and the information regarding the challenge chemical.

16 Claims, 4 Drawing Sheets

PERMEABILITY DETERMINATION

CROSS-REFERENCE TO RELATED APPLICATION

This application claims priority of British Patent Application No. 1311203.2, filed Jun. 24, 2013, the contents of which is incorporated herein by reference in its entirety.

BACKGROUND

This disclosure relates to permeability determination. In particular, but without limitation, this disclosure relates to methods and apparatuses for determining permeability of a material such as those employed in personal protective apparel.

Generally, most chemical protective clothing is tested to a common list of 21 chemicals, referred to as 'ASTM F1001-12 Standard Guide for Selection of Chemicals to Evaluate Protective Clothing Materials'.

Standard laboratory protocols for these tests include ASTM F739 and EN 374. ASTM F739 reports breakthrough time at 0.1 µg/min/cm$^2$ and Steady State Permeation (SSP) rate. EN 374 reports breakthrough time at 1.0 µg/min/cm$^2$ and SSP. Companies test further chemicals, in addition to the F1001 list.

The process of permeation through a material broadly involves three stages: firstly, molecules (in liquid or gas form) are absorbed onto the outer surface of the material; secondly, the molecules diffuse across the material or multiple layers of the material; and thirdly, desorption of the molecules from the inner surface of the material occurs. If the material is in the form of a protective garment, the molecules can come into contact with the wearer from the inner surface of the material.

However, test methods can vary between batches, laboratory, methodology and apparatus etc. Indeed, the differences observed between results on open and closed-loop apparatus are discussed in the ASTM F739 Standard.

BRIEF DISCLOSURE

Testing carried out by the inventor on an identical material in two different laboratories to ASTM F739 protocol resulted in vastly differing results, as shown in Table 1, below:

TABLE 1

| Chemical | CAS | ASTM F739 (0.1 µg/cm$^2$/min.) | Rate (µg/cm$^2$/min) |
|---|---|---|---|
| Acrylonitrile | 107-13-1 | 115 | 0.13 |
| | | >480 | <0.05 |
| Ammonia Gas | 7664-41-7 | >480 | 0.07 |
| | | 49 | 0.17 |
| Benzene | 71-43-2 | >480 | <0.02 |
| | | 35 | 3.00 |
| Carbon Disulfide | 75-15-0 | 178 | 0.10 |
| | | >480 | <0.05 |
| Chlorobenzene | 108-90-7 | 3 | 6.38 |
| | | 145 | 1.50 |
| n-Butyl Ether | 143-96-1 | 58 | 0.16 |
| | | >480 | <0.05 |
| Styrene | 100-42-5 | >342 | 0.42 |
| | | 208 | 0.51 (max) |
| Tetrahydrofuran | 109-99-9 | 320 | 0.17 |
| | | 27 | 4.10 |
| Toluene | 108-88-3 | >480 | <0.01 |
| | | 79 | 2.00 |

For each chemical listed in Table 1, the results in the first line were achieved in a first laboratory, and the results in the second line were achieved in a second laboratory.

Variable lab results (as demonstrated) suggest a more reliable and consistent method of reporting permeation rates would be beneficial to improving safety risk assessments, particularly for mission-specific conditions.

One issue with the results from standard testing protocols is that laboratory test data is not representative of usage situations. This is mainly due to differences in temperature, which influence permeation rate. Protective garments may be deemed unsuitable for certain uses when only standard laboratory testing data is referred to.

Therefore, there is a need for an improved method and apparatus for determining permeability of chemical protective or barrier materials such as those employed in personal protective apparel.

There is described herein a computer implemented method for determining a permeation breakthrough time and permeation rate of a chemical for a chemical protective material. This method may be carried out outside of a laboratory environment. This approach comprises the following steps: determining barrier characteristics of the material for which the breakthrough time and/or permeation rate is to be determined; retrieving information regarding the challenge chemical; selecting the temperature of the material for which the breakthrough time and/or permeation rate is to be determined; and using the temperature, the barrier characteristics, and the information regarding the challenge chemical, to determine how long the challenge chemical would take at the determined temperature to breakthrough a material having the barrier characteristics and/or to determine the permeation rate for the challenge chemical having the barrier characteristics at the determined temperature. Additionally, the method may further comprise selecting the percentage area of the chemical protective material subject to contamination.

The chemical protective material may be a homogenous or multi-layer film, membrane, laminate, coated fabric or fabric. The method may account for die composition, the thickness of the fabric and/or homogenous layer or thicknesses of each layer of the multi-layer material. The chemical protective material may be a chemical protective garment or suit.

The step of selecting the temperature of the material, garment or suit may be carried out by manual input by a user. Alternatively, the temperature may be automatically input by one or more temperature sensors. Additionally, the method may further comprise displaying a determined breakthrough time and/or permeation rate.

Preferably, the method may also determine a time of cumulative permeation to a predetermined volume. The cumulative permeation time may be compared with data comprised in predetermined toxicity tables, for example skin toxicity tables. The determined time of cumulative permeation and/or the predetermined skin toxicity ma additionally be displayed.

Additionally, the method may further include providing a timer with a configured timer setting, wherein the timer will sound an alarm once the permeation time and/for the time of cumulative permeation determined by the method is approached and/or reached and/or exceeded.

There is provided herein a mobile device operable to perform one or more of the methods described herein.

There is provided a computer readable medium carrying machine readable instructions arranged, upon execution by a processor, to cause one or more of the methods described herein to be carried out.

It is to be understood that other elements of the present disclosure will become readily apparent to persons skilled in the art from the following, detailed description, wherein various examples are shown and described by way of illustration.

Chemical breakthrough and permeation rate data assists safety professionals and users in evaluating different materials to ensure that appropriate chemical protective clothing, is selected for the task and duration of exposure. The methods described herein allow for the determination of the breakthrough raw of liquids, vapours and gases through chemical protection materials, including clothing materials, under continuous contact. Advantageously, whereas standard tests often show differing results between laboratories, laboratory procedures, test cells and samples, the methods and systems described herein are useful tools to improve the management of risk. The ability to determine the permeation rate and breakthrough time for a task-specific challenge chemical at a task-specific operating temperature presents a significant improvement to conventional methods of evaluating risks within a range of operating scenarios.

Permeation testing according to current standard practice is carried out at standard laboratory temperature; namely, at 23° C. However, it has been found that temperature has a significant influence on permeation rates of chemicals through material. This should be carefully considered when determining the suitability of chemical protection garment for a specified use.

Permeation of a chemical in a liquid, vapour, or gas form at normal body temperature of 37° C. will be higher than permeation at the standard test temperature of 23° C.

The steps of the methods described herein include: selecting operational parameters including, but not limited to: units (to report the results in either ASTM or EN Standards); suit type (selecting the suit type can provide an estimate for the surface area required for the calculations as each suit type is associated with a particular surface area); exposure time (period of time the user will be exposed to the challenge chemical, e.g. 1.5 hours where the slider is set at 90 minutes); safety factor (a "worst case" factor to allow for underestimation of diffusion factors); suit temperature (the temperature of the exposed suit, as temperature has a significant influence on the permeation rate); exposed area (the percentage area of the suit exposed to the challenge chemical); and/or air changes/hour (applies for air supplied suits only as if the suit is ventilated then the degree of exposure is reduced depending on air changes/hour). It will be appreciated that the suit temperature may differ from the standard laboratory temperature of 23° C. or normal body temperature of 37° C.

Additionally, there is a step of selecting the appropriate challenge chemical, e.g., by name or by CAS (Chemical Abstracts Service) number.

Thereafter, there is a step of calculating, by a processor, the predicted permeation of challenge chemicals. Optionally, there is a further step of reporting the calculated results; preferably, the following is reported:

breakthrough: The time to reach the ASTM limit of 0.1 µg/cm$^2$/min or the EN limit of 1.0 µg/cm$^2$/min, as selected. If breakthrough is not reached within the defined 'Exposure Time' the output shows ">exposure time".

permeation rate—This is the rate attained at the end of the time period in µg/cm$^2$/min. If the permeation has reached equilibrium, this is the steady state permeation rate;

permeated—The total amount that has permeated through the exposed area in µg; and/or optionally, the time to reach a specific volume of permeate e.g. "To 150 µg/cm$^2$"—If this value has not been reached the output shows ">exposure time". The actual limit for the specific challenge chemical (in this example 150 µg/cm$^2$) may be determined by a lookup toxicity table, which may be stored within a database.

BRIEF DESCRIPTION OF THE DRAWINGS

Examples will now be explained with reference to the accompanying drawings in which.

It will be appreciated that like reference numerals in the drawings indicate similar parts throughout the several views and several examples of the methods and systems described herein. It will also be appreciated that the Figures are illustrated by way of example, and not by way of limitation.

DETAILED DISCLOSURE

Figure 1:
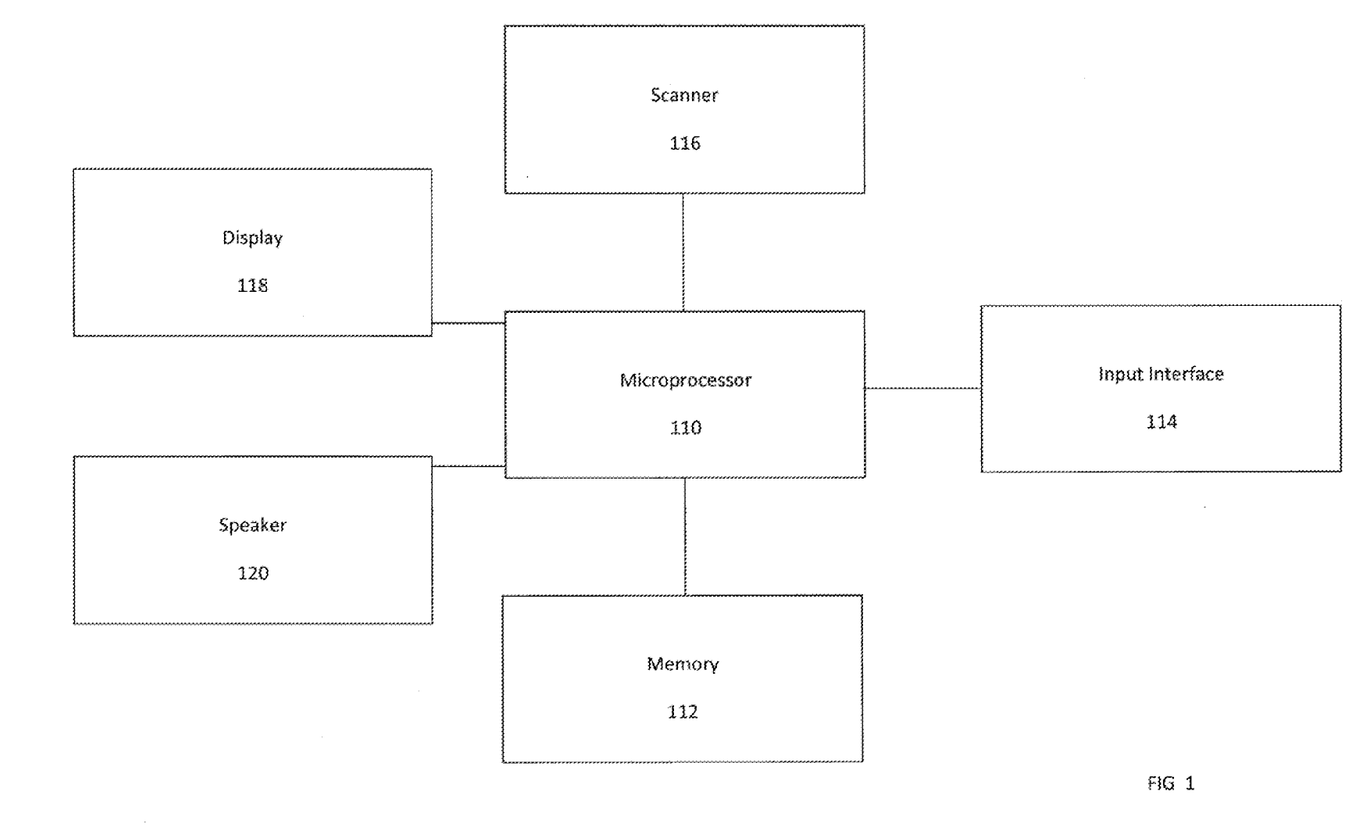
FIG. 1 shows an exemplary computing apparatus upon which the methods disclosed herein may be performed.

In FIG. 1, a microprocessor 110 is communicatively coupled to a memory 112 which is arranged to store instructions for execution on the microprocessor 110, the instructions optionally being in the form of an App. It will be appreciated that the instructions may be in any other suitable format known to the skilled person at the time of filing this application. The memory 112 is further arranged to store parameters that may be accessed by programs that are being run by the microprocessor 110, the parameters including but not limited to one or more chemical parameters that may be employed by the microprocessor 110 to determine permeability of a material. The parameters may be stored in the form of a database or structured as a table including one or more parameter entries for each of one or more different chemicals.

The microprocessor 110 is further coupled to an input interface 114 which may take the form of one or more of buttons, a keyboard, a touch sensitive display, an antenna, a USB port, etc. The input interface 114 is arranged so that information may be provided to the microprocessor 110, for example so as to provide an indication of a specific chemical, a particular material, or an item of personal protective clothing, etc. Preferably, the microprocessor 110 is further coupled to a scanner 116 which may take the form of a quick response scanner, QRS, or barcode scanner, arranged to scan a barcode or QRS code so that information relating to the foregoing may be provided to the microprocessor 110 thereby.

Optionally, the microprocessor 110 is further coupled to a display 118 arranged to display information in response to the execution of instructions by the microprocessor 110. The display 118 may be a touch sensitive display in which case it may be incorporated with the input interface 114. Additionally or alternatively, the microprocessor 110 is optionally coupled to a speaker 120 arranged to generate an audio signal when instructed to by the microprocessor 110.

Where the methods described herein are implemented as application on a mobile device, such as a mobile telephone device, a tablet, laptop, mobile computer, PDA, or any other portable device, it will be appreciated that the microprocessor 110 and the memory 112 need not be external, but rather these components may be integral with the mobile device. The input interface 114, in this example, can be buttons on the mobile device or the touchscreen, etc. Additionally, the display 118, and optionally the speaker 120, may also form an integral part of the mobile device. Additionally, a camera on a mobile phone may be used as the scanner 116 such that a picture may be taken of a barcode or QR code, the information from which may be decoded by the microprocessor 110 for processing.

It will be appreciated that each of the components described above in respect of FIG. 1 can be integrated into one apparatus or can be components of multiple devices which work together. It will also be appreciated that any such apparatus may be implemented using general purpose computer equipment or using bespoke equipment.

The hardware elements, operating systems and programming languages of such computers are conventional in nature, and persons skilled in the art will be adequately familiar therewith.

Figure 2:
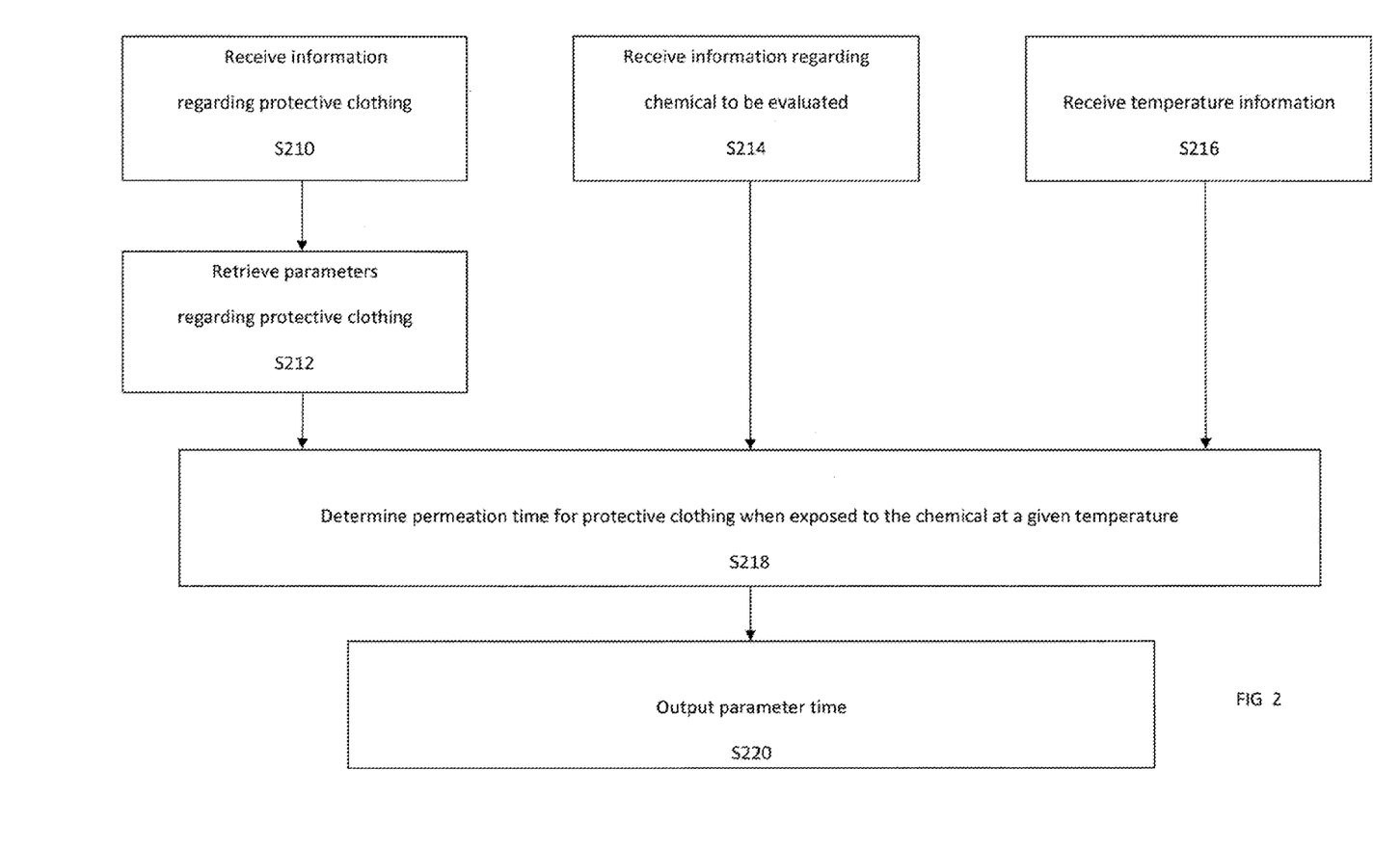
FIG. 2 shows a flow chart representative of an exemplary method of the present disclosure.

FIG. 2 shows a flow chart of an exemplary method described herein. At step S210 information is received regarding a protective material or clothing that is to be assessed. As an example, a user may manually input information via the input interface 114 or in the event that the protective clothing carries a barcode or QR code, the user may use the scanner 116 to scan the barcode or QR code so as to provide the microprocessor 110 with the information regarding the protective clothing.

At step S212, the microprocessor 110 retrieves from the memory 112 parameters relating to the specific material or clothing that is to be assessed. At step S214, information is received regarding the chemical for which the permeation time is to be evaluated for the protective clothing. The information may be received by a user indicating a particular chemical via the input interface 114. Another additional or alternative possibility is that the microprocessor 110 may receive information regarding one or more chemicals from the memory 112 in order for the microprocessor 110 to evaluate permeation times for one or more chemicals. It will also be appreciated, that the information regarding the chemical that is to be considered may optionally be received by the microprocessor 110 from either an integrated or an external detector (not shown); the detector comprising means to detect one or more chemicals.

At step S216, information is received regarding a temperature at which the permeation time is to be assessed. The temperature information may be provided by way of the user providing information via the input interface 114. As one possibility, the microprocessor 110 may be coupled to a temperature sensor (not shown) arranged to sense a temperature for which the permeation time is to be determined. At step S218, the microprocessor 110 determines a permeation time for the protective clothing when it is exposed to the chemical for which information was received at step S214 and when it is at the temperature for which information was received at step S216.

The memory 112 contains a database of key characteristics and molecular properties of each chemical. The key parameters for diffusion which may be contained in the database including, but not limited to the following, are:

Diffusion Coefficients

Diffusion coefficients for each polymer component of the barrier are determined by gravimetric absorption tests measuring the uptake of indicator chemicals in the constituent polymers and where available, look-up tables of the diffusion coefficients.

Diffusion Factor

Diffusion factors account for molecular shape since branched molecules diffuse more slowly than linear molecules of the same molar volume (MVol).

Molar Volume

The larger the molar volume (MVol), the slower the diffusion. This is further modified by the Diffusion factor above.

Temperature Relationship

The Diffusion coefficient is calculated using an industry standard temperature dependence of diffusion. Diffusion coefficients for each permeate are estimated for 25° C. and then modified for the specified temperature.

Fickian Diffusion

The microprocessor 110 automatically handles the complexities of solving the differential equations of diffusion. With the calculated solubilities at each interface plus the temperature-corrected diffusion coefficients, the microprocessor 110 calculates permeation rates through the whole system. Diffusion coefficients are dependent on the percentage of chemical in the polymer—the higher the percentage the more "open" the polymer is and the faster the diffusion. In the microprocessor 110 a factor of 1000 is assumed between the diffusion coefficient at 0% solvent up to 30% solvent—and then the rate is assumed constant.

Hansen Solubility Parameters (HSP)

The key insight is that "like dissolves like" and the definition of "like" is encoded in the three HSP $\delta D$, $\delta P$, $\delta H$ which encapsulate Dispersion, Polar and Hydrogen bonding. If all three HSPs of a chemical match reasonably well with those of a polymer then the chemical is soluble in the polymer. If there is a large mismatch of one or more HSP, then the solubility is low.

Infinite Source

An assumption may be made that the challenge chemical is present in infinite amounts—i.e. that the chemical that diffuses through the barrier is instantly replenished on the outside.

At S220, the microprocessor 110 outputs a permeation breakthrough time and rate. The permeation breakthrough time and rate may be output via the display 114. In another possibility the microprocessor 110 may drive the speaker 120 to provide an audio indication of the permeation breakthrough time and/or rate.

Figure 3:
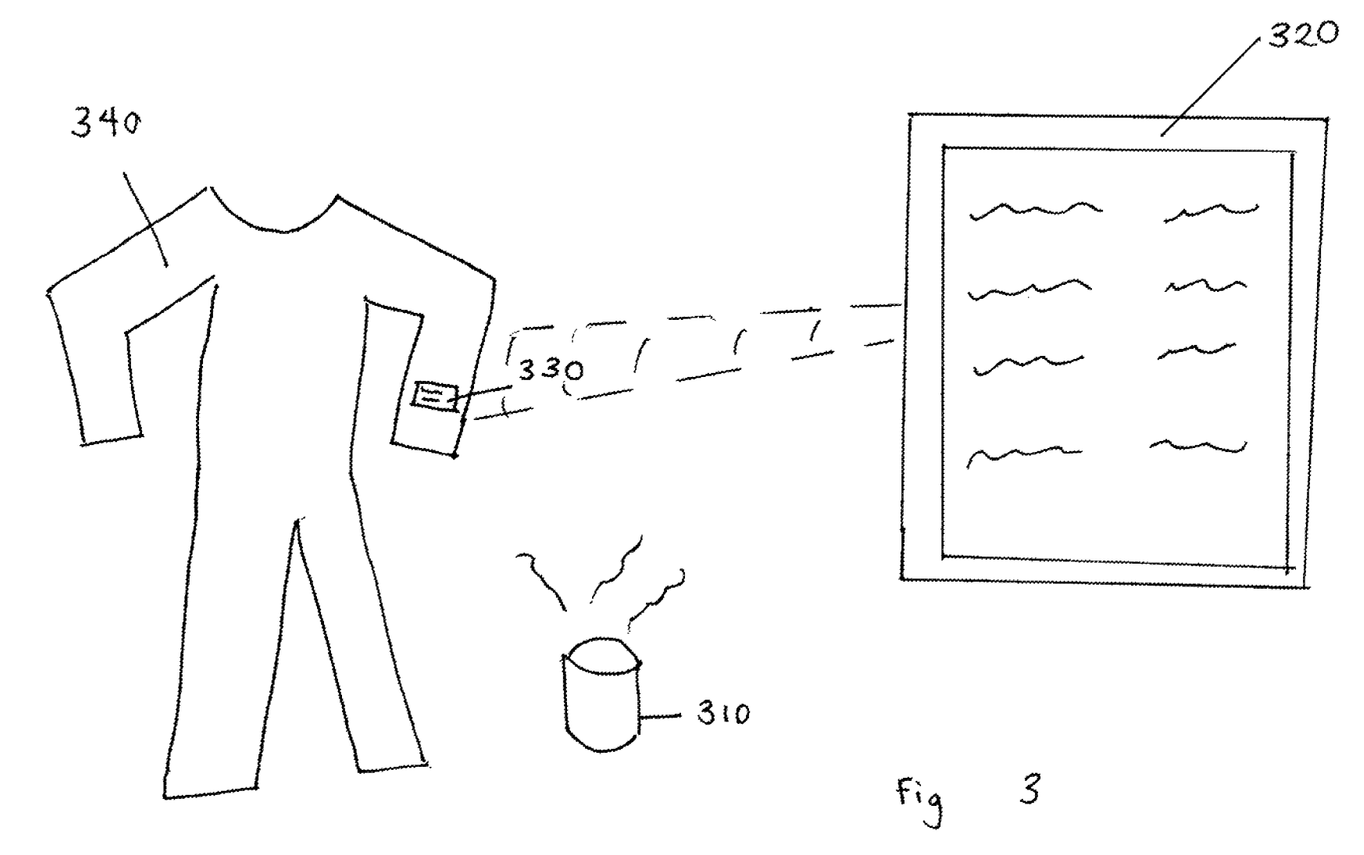
FIG. 3 shows a further example of a device being employed in conjunction with personal protective clothing.

FIG. 3 illustrates an approach wherein, prior to approaching a known chemical 310, a user uses a device 320, in this case a tablet, or a mobile device or similar, to scan QR code 330 on an item of personal protective clothing 340 (in this case an over-suit). Once the user has provided information regarding the chemical 310, by manual input or otherwise, and preferably, the suit temperature, the device 320 outputs a permeation breakthrough time and rate and a period of time for which it would be acceptable for a user working at that temperature and wearing the clothing 340 to be exposed to the chemical 310. In one example, details regarding the chemical 310 can be provided to the device 320 by taking an image of the chemical, e.g. a label, chemical name of or barcode on the chemical, and the microprocessor 110 may utilise optical character recognition software to determine the chemical to be assessed—thereby providing the device 320 with the information regarding the chemical 310 without requiring manual user input.

Optionally, the device 320 may also start a timer running so that, once the exposure time is approached or exceeded, an alarm is sounded by the speaker 120 so as to indicate to the wearer of the clothing 340 that they need to remove themselves from the vicinity of the chemical 310. It will be appreciated that the alarm may be set at predetermined intervals before the permeation time has elapsed in order to give the wearer of the clothing 340 adequate warning. These predetermined intervals will preferably be adjusted depending on the toxicity of the chemical to be assessed; i.e. adjusted for longer durations for chemicals of higher toxicity.

Figure 4:
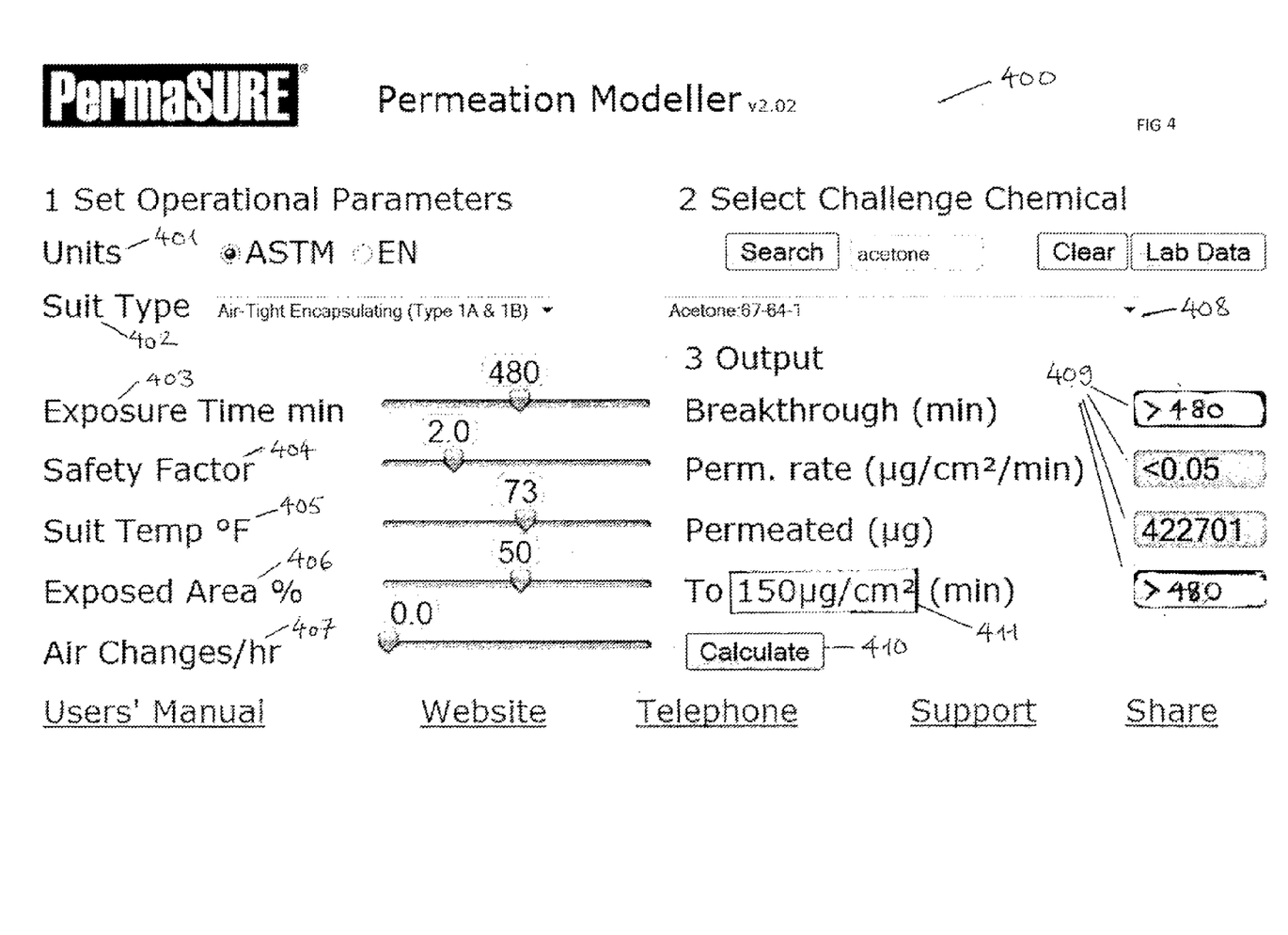
FIG. 4 shows an example screen shot of a device performing a method as described herein.

FIG. 4 shows an example user interface of a device arranged to perform a method as described herein. A graphic user interface 400 allows a user to select the units for the operational parameters 401 as either ASTM or EN. A drop down menu is provided to allow a user to select the particular suit type 402. In this example, a 'coverall hooded' suit has been selected in field 402. Suit types include, but are not limited to, coverall without hood, coverall hooded, air-tight encapsulating, and air-tight non-encapsulating. The suit type field 402 is used to provide an estimate of the surface area required for calculating the speed of permeability.

As illustrated, the user can optionally manually set a minimum exposure time in field 403 thereby allowing a user to set a period of time for which they believe they will be exposed to the chemical to be assessed. If a value has been input in the minimum exposure time limit field 403 which, on calculation, exceeds the output parameter time calculated at step S220, preferably, the device displays an indication and/or sounds an alarm signal to indicate that the breakthrough time is less than the exposure time.

At field 404, the user can input a safety factor. The safety factor allows a user to establish a "worst case" scenario to allow for underestimation of diffusion factors. Preferably, where the "worst case" scenario is selected in 404, illustrated by selecting 1.0, two alarms can be raised. The first of which sounds when the "worst case" scenario has been reached and the second is sounded when the estimated breakthrough time is reached. Optionally, a countdown timer starts from when the first alarm is raised, so that the wearer can obtain a visual and/or audio alert from the display 118 or speaker 120 of the device 320 to indicate the amount of time available before breakthrough. It will be appreciated that these indications can be provided on the display 118 and/or using the speaker 120.

In the suit temperature field 405, the user is able to input the temperature of the exposed suit. It will also be appreciated that the suit temperature field 405 may be automatically determined by the microprocessor 110 when the microprocessor 110 is connected to, or is operable to receive information from one or more temperature sensors (not shown). Although in this example the temperature is indicated in degrees Fahrenheit, it will be appreciated that any other unit of temperature, such as degrees Celsius, can be used.

The user may optionally also include the percentage area of the material, e.g., suit, exposed to the liquid chemical in Exposed Area % field 406. This percentage is determined by whether the chemical is in the gas phase (e.g. 100% exposure), or vapour phase, or in the liquid phase. For a chemical in liquid form, the exposure can be estimated by e.g. contact with the front of the chemical suit. The exposed area is related to the amount of chemical that is available to permeate through the material. Optionally, the user may include details about the number of air changes per hour in field 407 as the degree of exposure is reduced if the suit is highly ventilated; i.e. has a high number of an changes/hour. Field 407 is available for an supplied suits only and may therefore be greyed out, or otherwise unavailable, when the air supplied suits option is not selected in suit type field 402.

The type of chemical may be selected in field 408 using the drop down menu. Alternatively, this information may be automatically provided by the microprocessor 110. The one or more parameters in field 409 may be manually input by the user or provided by microprocessor 110. It will be appreciated that in other examples, these parameters 109 are not displayed, such that when the type of chemical is input in field 408, the only parameter which may be displayed will be the output time which indicates permeation time as calculated by the microprocessor 110 for the protective clothing when exposed to the given chemical at the specified temperature. Alternatively, as is illustrated in FIG. 4, a further button 410 may be provided which, when selected, calculates the breakthrough time and displays the result. The result may be displayed on a separate user interface, for example as a pop-up, or may be displayed in the graphic user interface 400 of FIG. 4.

Although in the example of FIG. 4, the graphic user interface 400 includes slide bars, drop down menus and selection buttons for various fields, it will be appreciated that each field can be presented in a manner of suitable formats, including but not restricted to these three options.

The particular operating parameters provided in the example shown in the graphic user interface 400 of FIG. 4 are provided below in a tabular format:

TABLE 2

|  | ASTM F739 | EN 374 |
| --- | --- | --- |
| Suit Type | Coverall hooded | Coverall hooded |
| Exposure Time | 120 [0-960] | 120 [0-960] |
| Safety Factor | 2.0 [1-5] | 2.0 [1-5] |
| Operating Temperature | 73° F. [39-104] | 23 [4-40]° C. |
| Exposed Area | 15% [1-100] | 15% [1-100] |
| Air Changes per Hour | Only usable if Air Supplied Suit is selected, default = 4 | Only usable if Air Supplied Suit is selected, default = 4 |

Although in the example detailed in FIG. 4, the predetermined toxicity limit is set to 150 $\mu g/cm^2$, it will be appreciated that other values can be used. Alternatively, the predetermined toxicity limit can be manually or automatically be set in the cumulative permeation field 411 using the toxicity classification system from EU Regulation No 1272/2008 on classification, labelling and packaging of substances and mixtures, which is hereby incorporated by reference in its entirety, as set out in Table 3.1.1 therein (on page 81), which may be stored in the memory 112. Although this particular toxicity classification system is used, it will be appreciated that any toxicity classification system can be utilized and furthermore the details in this table can be updated or modified otherwise.

In this example and with the predetermined toxicity limit, the method can further determine the time to cumulative permeation; which is the time it takes a pre-defined amount of chemical to permeate 1 $cm^2$ of material. The pre-defined amount may be set according to the skin toxicity of the chemical as per the illustrative example set out in the table below:

TABLE 3

| Dermal Toxicity Classification (short or long term) | Cumulative permeation (in µg/cm2): |
|---|---|
| Very Toxic: | |
| Category 1, or Classified as Carcinogen, mutagen, or reproductive toxicants (CMR) Skin sensitisers | 20 |
| Toxic: | |
| Category 2 All other chemicals | 75 |
| Unknown classification, Category 3, or 4 | 150 |

In this example, when the time to cumulative permeation is determined, the device can additionally display this value with an additional indication of the determined toxicity; for example, using the labels "Unknown", "Low risk", "Toxic" and "Very Toxic". In view of the fact that above exemplified toxicity classification system is a European classification system, this additional step of determining and/or displaying the toxicity level is particularly preferable. It will be appreciated that other classification systems can also be utilised in a similar manner.

The methods described herein may be displayed on a computer and stored in the form of computer readable instructions that, when executed on a processor of a computer, cause the methods described herein to be carried out. Examples of media upon which instructions may be stored include, but are not limited to, magnetic discs, optical discs, solid state memory—for example in the form of USB stick etc. The instructions may also be provided by way of a signal such as an optical or radio signal upon which the instructions are encoded.

The methods may be executed on a mobile station and/or on a computing device such as a server. Program aspects of the technology can be thought of as "products" or "articles of manufacture" typically in the form of executable code and/or associated data that is carried on or embodied in a type of machine readable medium. "Storage" type media include any or all of the memory of the mobile stations, computers, processors or the like, or associated modules thereof, such as various semiconductor memories, tape drives, disk drives, and the like, which may provide storage at any time for the software programming. All or portions of the software may at times be communicated through the Internet or various other telecommunications networks. Such communications, for example, may enable loading of the software from one computer or processor into another computer or processor.

Non-volatile storage media include, for example, optical or magnetic disks, or the like. Volatile storage media include dynamic memory, such as the main memory of a computer platform. Tangible transmission media include coaxial cables; copper wire and fibre optics, including the wires that comprise the bus within a computer system. Carrier-wave transmission can take the form of electric or electromagnetic signals, or acoustic or light waves such as those generated during radio frequency (RF) and infrared (ER) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a FRAM, a PROM and EPROM, a FLASH-EPROM, any other memory chip or cartridge, or any other medium from which a computer can read programming code and/or data. Many of these forms of computer readable media may be involved in carrying one or more sequences of one or more instructions to a processor for execution.

As detailed above, herein described is a computer implemented method for determining the breakthrough time of a chemical through a chemical protective material. The chemical protective material may be a membrane, a laminate, coated material or a material.

The chemical protective material may be provided as a chemically protective garment, or suit, with or without an air supply option, or may be provided as a chemically protective material for protecting objects from exposure to a chemical.

The methods described herein may be performed on a portable device, such as a scanner with a CPU, a mobile device, and/or any other suitable device.

The portable nature of the device 320 has the advantage that the permeation of a chemical can be determined on site, at the time that this is required and taking into account the conditions under which the chemical will be used, e.g. temperature, the form of the chemical, liquid, vapour, or gas phase, and the exposure level of the user.

The methods described herein therefore do not need to be carried out in a laboratory under standard laboratory conditions. This presents the significant advantage that the environment of exposure to a chemical can be assessed and allows the direct calculation of the breakthrough time of the chemical for a protective garment. For example, the appropriate temperature, chemical, form of the chemical (e.g. in liquid, vapour, or gas form), are assessed and taken into account.

By entering the relevant garment type and usage conditions (exposure period, suit type, material or garment temperature, suit area exposed/contaminated) and a safety factor, the user can quickly determine breakthrough time, steady state permeation rate and cumulative permeation of the chemical through the material.

The material may, for example, the Powerply® chemical resistant material, such as Powerply® BF01, which can be used to manufacture protective clothing or protective membranes or sheets.

The methods described herein allow known toxicity data stored in a database to be used in the determination of the level of risk, and the maximum safe period of exposure.

The methods described herein may use Hansen Solubility parameters of chemicals. The parameters for each chemical are stored in a database. The parameters take into consideration the energy in a particular chemical from: dispersion forces, dipolar intermolecular forces and hydrogen bonds between molecules.

Exemplary Hansen Solubility parameters are set out below in Table 4 (taken from Hansen Solubility Parameters in Practice):

TABLE 4

| Chemical | δD | δP | δH |
|---|---|---|---|
| Acetaldehyde | 14.7 | 12.5 | 7.9 |
| Acetaldoxime | 16.3 | 4 | 20.2 |
| Acetamide | 17.3 | 18.7 | 19.3 |
| Acetanilide | 20.6 | 14.4 | 13.5 |
| Acetic Acid | 14.5 | 8 | 13.5 |
| Acetic Anhydride | 16 | 11.7 | 10.2 |
| Acetone | 15.5 | 10.4 | 7 |

TABLE 4-continued

| Chemical | δD | δP | δH |
|---|---|---|---|
| Acetonecyanhydrin | 16.6 | 12.2 | 15.5 |
| Acetonemethyloxime | 14.7 | 4.6 | 4.6 |
| Acetonitrile | 15.3 | 18 | 6.1 |
| Acetophenone | 18.8 | 9 | 4 |
| Acetoxime | 16.3 | 3.7 | 10.9 |
| Acetyl Salicylic Acid | 19 | 6.9 | 9.7 |

The apparatus described herein can be applied at operating temperatures above, at, or below the standard laboratory test temperature of 23° C. This allows the body temperature of a user to be taken into account and also allows local ambient conditions (e.g. outside temperature) to be taken into account, for example, hot and cold environmental conditions.

In one example of the method described herein, for fabric A, the breakthrough time to a user-chosen limit of 100 µg/cm$^2$ for acetone is calculated as follows, using the solubility of the chemical in the material, for example, in the outermost layer of the material estimated from the HSP Distance value:

$$\text{Distance} = \text{Sqrt}(4(\delta D_1 - \delta D_2)^2 + (\delta P_1 - \delta P_2)^2 + (\delta H_1 - \delta H_2)^2)$$

where $\delta D_1$, $\delta D_2$, etc. are the Hansen Solubility Parameters of the chemical and the material and then using numerical integration (via discrete time steps) of the Fickian diffusion equation:

$$\delta C/\delta t = D \delta^2 C/\delta^2 x$$

which states that the rate of change of concentration, C, with time, t, is given by the diffusion coefficient, D, multiplied by the second derivative of the concentration gradient, C/x.

Values of diffusion coefficients fix typical materials used can be stored in the memory 112 of the device 320. The breakthrough time is determined when the value of δC/δt at the inside of the material layer exceeds the specified limit (e.g. 1 µg/cm$^2$/min).

TABLE 5

| | Acetone | | |
|---|---|---|---|
| Temperature | Permeation Rate µm/cm$^2$/min | Permeated µm | Mins to reach 100 µm/cm$^2$ |
| 23° C. | 2.02 × 10$^{-1}$ | 5.79 × 10$^3$ | >480 |
| 37° C. | 4.51 × 10$^{-1}$ | 7.76 × 10$^8$ | 245 |

The results for permeation at 37° C. are that the 100 µg/cm$^2$ limit is reached in just over half the time taken at 23° C.

Table 6, below, shows test data for Powerply® BF01 material at 23° C.

TABLE 6

| Chemical Resistance | CAS No. | State | Breakthrough ASTM F739 0.1 µg/ (min · cm$^2$) | Breakthrough EN 374 1.0 µg/ (min · cm$^2$) | Units | Performance Level |
|---|---|---|---|---|---|---|
| Acetone | 67-64-1 | Liquid | >480 | >480 | minutes | Class 6 |
| Acetonitrile | 75-05-8 | Liquid | >480 | >480 | minutes | Class 6 |
| Ammonia Gas | 7664-41-7 | Gas | >45 | >480 | minutes | Class 6 |
| 1,3-Butadiene Gas | 106-99-0 | Gas | >480 | >480 | minutes | Class 6 |
| Carbon Disulphide | 75-15-0 | Liquid | >480 | >480 | minutes | Class 6 |
| Chlorine Gas | 7782-50-5 | Gas | >480 | >480 | minutes | Class 6 |
| Dichloromethane | 75-09-2 | Liquid | >480 | >480 | minutes | Class 6 |
| Diethylamine | 109-89-7 | Liquid | >9 | >10 | minutes | Class 1 |
| Dimethyl Formamide | 68-12-2 | Liquid | >480 | >480 | minutes | Class 6 |
| Ethyl Acetate | 141-78-6 | Liquid | >480 | >480 | minutes | Class 6 |
| Ethylene Oxide Gas | 75-21-8 | Gas | >480 | >480 | minutes | Class 6 |
| n-Hexane | 110-54-3 | Liquid | >480 | >480 | minutes | Class 6 |
| Hydrogen Chloride Gas | 7647-01-0 | Gas | >480 | >480 | minutes | Class 6 |
| Methanol | 67-56-1 | Liquid | >50 | >480 | minutes | Class 6 |
| Methyl Chloride Gas | 74-87-3 | Cas | >480 | >480 | minutes | Class 6 |
| Nitrobenzene | 98-95-3 | Liquid | >480 | >480 | minutes | Class 6 |
| Sodium Hydroxide, 50% | 1310-73-2 | Liquid | >480 | >480 | minutes | Class 6 |
| Sulphuric Acid, 98% | 7664-93-9 | Liquid | >480 | >480 | minutes | Class 6 |
| Tetrachloroethylene | 127-18-4 | Liquid | >480 | >480 | minutes | Class 6 |
| Tetrahydrofuran | 109-99-9 | Liquid | >20 | >40 | minutes | Class 2 |
| Toluene | 108-88-3 | Liquid | >5 | >20 | minutes | Class 1 |

The invention claimed is:

1. A method for determining a time for a challenge chemical to cumulatively permeate through a chemical protective material to a toxicity limit, the method comprising:
   retrieving, with the processor, barrier characteristics of the chemical protective material from a computer memory;
   obtaining, with the processor, information regarding the challenge chemical, the information including a toxicity limit for the challenge chemical;
   receiving, at the processor, a temperature of the chemical protective material for which the time is to be determined; and
   using the temperature, the barrier characteristics, and the information regarding the challenge chemical, to determine a time for the cumulative permeation of the challenge chemical through the material to reach the toxicity limit at the received temperature.

2. The method according to claim 1, wherein determining the time for the cumulative permeation of the challenge chemical through the material to reach the toxicity limit comprises determining the permeation rate for the challenge chemical through the chemical protective material at the received temperature.

3. A computer implemented method according to claim 1, wherein the receiving of the temperature of the material is manually input by a user.

4. A computer implemented method according to claim 1, wherein the receiving of the temperature of the material comprises determining of the temperature by one or more temperature sensors.

5. The method according to claim 1, wherein the method is implemented outside of a laboratory environment laboratory environment.

6. The method according to claim 1, wherein the chemical protective material is a homogenous or multi-layer film, membrane, laminate, coated fabric or fabric.

7. The method according, to claim 1, wherein the chemical protective material is a chemical protective garment or suit.

8. The method according to claim 1, further comprising receiving a selection of a percentage area of the chemical protective material subject to contamination by the challenge chemical.

9. The method according to claim 1, further comprising operating a display to present the determined time for the cumulative permeation of the challenge chemical through the material to reach the toxicity limit at the receiving temperature.

10. The method according to claim 1, wherein the time for the challenge chemical to cumulatively permeate through the chemical protective material to the toxicity limit is calculated based on a predetermined skin toxicity of a challenge chemical.

11. The method according to claim 1, wherein the method further includes providing a timer, wherein the timer will sound an alarm once the permeation time determined by the method is approached and/or reached and/or exceeded.

12. An apparatus for determining a time for a challenge chemical to cumulatively permeate through a chemical protective material to a toxicity limit, the apparatus comprising:
a memory comprising barrier characteristics for a plurality of chemical protective materials;
an input interface that receives a selection of the chemical protective material from the plurality of chemical protective materials;
a microprocessor communicatively connected to the memory and the input interface, the microprocessor configured to:
retrieve at least one barrier characteristic of the chemical protective material from the memory;
obtain information regarding a challenge chemical, the information including a toxicity limit for the challenge chemical;
obtains a temperature of the chemical protective material for which the time is to be determined; and
determine the time for the cumulative permeation of the challenge chemical through the material to reach the toxicity limit at the selected temperature using the temperature, the barrier characteristics, and the information regarding the challenge chemical; and
a display operable by the microprocessor to the present the determined time.

13. The apparatus of claim 12, further comprising a temperature sensor communicatively connected to the microprocessor wherein the microprocessor obtains the temperature of the chemical protective material from the temperature sensor.

14. The apparatus of claim 12 further comprising a chemical detector communicatively connected to the microprocessor wherein the microprocessor obtains the information regarding the challenge chemical based upon an indication received from the chemical detector.

15. A non-transient computer readable medium programmed with computer readable codes that upon execution by a microprocessor, causes the microprocessor to:
retrieve at least one characteristic of a chemical protective material from a computer memory;
obtain information regarding a challenge chemical, the information including a toxicity limit for the challenge chemical;
receive a temperature of the chemical protective material at which the time is to be determined; and
use the temperature, the at least one characteristic, and the information regarding the challenge chemical, to determine a time for the cumulative permeation of the challenge chemical through the material to reach the toxicity limit at the receiving temperature.

16. The non-transient computer readable medium of claim 15, wherein determining the time for the cumulative permeation of the challenge chemical through the material to reach the toxicity limit comprises determining the permeation rate for the challenge chemical through the chemical protective material at the received temperature.

* * * * *